(12) United States Patent
Tobia

(10) Patent No.: US 9,192,519 B2
(45) Date of Patent: *Nov. 24, 2015

(54) SPORTS GOGGLE

(75) Inventor: Michael Stephen Tobia, Carlsbad, CA (US)

(73) Assignee: Dragon Alliance, LLC, San Clemente, CA (US)

( * ) Notice: Subject to any disclaimer, the term of this patent is extended or adjusted under 35 U.S.C. 154(b) by 316 days.

This patent is subject to a terminal disclaimer.

(21) Appl. No.: 13/530,884

(22) Filed: Jun. 22, 2012

(65) Prior Publication Data

US 2012/0324638 A1    Dec. 27, 2012

Related U.S. Application Data

(60) Provisional application No. 61/501,154, filed on Jun. 24, 2011.

(51) Int. Cl.
*A61F 9/02*    (2006.01)
*G02C 9/00*    (2006.01)

(52) U.S. Cl.
CPC . *A61F 9/02* (2013.01); *A61F 9/025* (2013.01); *G02C 9/00* (2013.01); *A61F 9/028* (2013.01); *A61F 2210/009* (2013.01)

(58) Field of Classification Search
CPC ..... A61F 9/025; A61F 2210/009; A61F 9/02; A61F 9/028; G02C 9/04; G02C 9/00
USPC ............. 2/439, 441, 426, 452; 351/83, 86, 92
See application file for complete search history.

(56) References Cited

U.S. PATENT DOCUMENTS

| 3,718,937 A | | 3/1973 | Smith | |
|---|---|---|---|---|
| 3,896,496 A | * | 7/1975 | Leblanc et al. | 2/439 |
| 3,931,646 A | * | 1/1976 | Loughner | 2/452 |
| 4,977,627 A | | 12/1990 | Metcalfe et al. | |
| 5,363,512 A | * | 11/1994 | Grabos et al. | 2/436 |

(Continued)

FOREIGN PATENT DOCUMENTS

GB    2470419    * 11/2010

OTHER PUBLICATIONS

International Search Report, dated Sep. 13, 2012, from corresponding International Application Serial No. PCT/US2012/043802.

(Continued)

*Primary Examiner* — Anna Kinsaul
(74) *Attorney, Agent, or Firm* — Brient Globerman, LLC

(57) ABSTRACT

An interchangeable lens assembly including a first lens, a lens bracket coupled to the first lens, and at least one connection portion disposed around at least a portion of a perimeter of the lens bracket. A goggle including a goggle frame and at least one coupling point disposed on the goggle frame and adapted to couple to the at least one connection portion on the lens bracket. The at least one coupling point and the at least one connection portion may be corresponding magnetic portions adapted to couple to each other by a magnetic interaction, and/or the at least one connection portion may be a protrusion, and the at least one coupling point may be an aperture adapted to receive and couple to the protrusion. This allows the lens assembly to be attached to and detached from the goggle frame quickly and easily with reduced manual dexterity.

21 Claims, 15 Drawing Sheets

(56) References Cited

U.S. PATENT DOCUMENTS

| | | | |
|---|---|---|---|
| 5,542,130 A | | 8/1996 | Grabos, Jr. et al. |
| 5,689,834 A | | 11/1997 | Wilson |
| D427,225 S | * | 6/2000 | Arnette ............ D16/312 |
| 6,601,240 B2 | | 8/2003 | Tsubooka |
| 6,637,038 B1 | * | 10/2003 | Hussey ............ 2/436 |
| 7,891,025 B2 | * | 2/2011 | Kobayashi et al. ............ 2/436 |
| 2007/0261155 A1 | * | 11/2007 | Tabacchi ............ 2/439 |
| 2009/0222979 A1 | | 9/2009 | Wang |
| 2009/0257019 A1 | | 10/2009 | Dichiara |
| 2010/0064421 A1 | | 3/2010 | Wang-Lee |

OTHER PUBLICATIONS

Written Opinion of the International Searching Authority, dated Sep. 13, 2012, from corresponding International Application Serial No. PCT/US2012/043802.

International Preliminary Report on Patentability, dated Dec. 24, 2013, from corresponding International Application Serial No. PCT/US2012/043802.

* cited by examiner

SPORTS GOGGLE

CROSS REFERENCES TO RELATED APPLICATIONS

This application claims the benefit of U.S. Provisional Patent Application Ser. No. 61/501,154 entitled SNOW AND SAND GOGGLE, filed on Jun. 24, 2011, the contents of which are expressly incorporated herein by reference in its entirety.

FIELD

The present disclosure generally relates to a goggle, and more specifically to a goggle with an increased peripheral vision and a mechanism for switching lenses.

BACKGROUND

Snow and sand goggles and their variations have been around for many years. There are many kinds of goggles used by skiers, snowboarders, motocross, and ATV riders to help their vision remain clear while they are in the process of their activities. Goggles have continued to evolve including new aesthetic and functional features. The standard goggle consists of a frame and a secured lens which is permanently attached to the frame. Recently, there have been some goggles developed which enable the user to replace the viewing lens. The current replaceable lens technology can be burdensome and difficult to manipulate, especially with a gloved hand while in the field, and typically requires the user to remove the glove and/or leave the field to change the lens. Additionally, the basic framework around the typical ski goggle creates a seal around the face but also results in a decreased peripheral viewing ability.

SUMMARY

The embodiments disclosed herein generally relate to new protective goggles, for example, sports goggles and snow and sand goggles, including a frame designed to increase the peripheral viewing abilities of the user and have sufficient support to enable a lens to be easily attached, detached, and reattached quickly and easily without substantial tactile resources.

In an illustrative embodiment, the lens technology disclosed herein is an application of lens to frame techniques which utilize a male system of coupling interfaces located on peripheral edges of the lens to adhere the lens to the frame via interaction of the male interfaces with female receivers located on the frame. In another illustrative embodiment, the lens technology utilizes magnetic coupling interfaces located on peripheral edges of the lens to adhere the lens to the frame via interaction of the magnetic coupling interfaces with corresponding magnetic coupling interfaces located on the frame.

In an illustrative embodiment, a goggle assembly and interchangeable lens assembly is disclosed herein. The interchangeable lens assembly includes a first lens having a first surface and a second surface opposite the first surface, and a lens bracket having a first coupling surface and a second coupling surface opposite the first coupling surface. The first coupling surface of the lens bracket is coupled to the second surface of the first lens. The lens bracket also includes at least one connection portion disposed around at least a portion of a perimeter of the second coupling surface of the lens bracket. The goggle assembly includes a goggle frame including a first side and a second side opposite the first side, and at least one coupling point disposed on the first side of the goggle frame. The at least one coupling point of the goggle frame is adapted to couple to the at least one connection portion on the lens bracket. In one embodiment, the at least one coupling point and the at least one connection portion are corresponding magnetic portions adapted to couple to each other by a magnetic interaction. In another embodiment, the at least one connection portion includes at least one protrusion, and the at least one coupling point includes at least one aperture adapted to receive and couple to the at least one protrusion.

These embodiments provide a frameless design aesthetic from a front view, and an increased peripheral viewing range for the user without the need to expand the size of the traditional frame material. Based on the frame and lens coupling designs disclosed herein the goggles provide an increased field of vision without increasing overall product size, and also provide an easier, more efficient user experience to interchange lenses.

BRIEF DESCRIPTION OF THE DRAWINGS

Embodiments of goggles are illustrated in the figures of the accompanying drawings which are meant to be exemplary and not limiting, in which like references are intended to refer to like or corresponding parts, and in which.

DETAILED DESCRIPTION

Detailed embodiments of goggles, for example, sports goggles and snow and sand goggles, are disclosed herein, however, it is to be understood that the disclosed embodiments are merely exemplary of the goggles, which may be embodied in various forms. Therefore, specific functional details disclosed herein are not to be interpreted as limiting, but merely as a basis for the claims and as a representative basis for teaching one skilled in the art to variously employ the present disclosure.

In illustrative embodiments, enhanced view replaceable lens sports goggles that may be used for skiing, snowboarding, motocross, snowmobiling or any other sports where eye protection and visibility is important are disclosed herein. The enhanced view replaceable lens goggles provide an increased field of vision as compared to other goggles and thus have the ability to provide a greater level of protection in that a wearer or user may be able to identify hazards that the user may otherwise not have identified when wearing other goggles. Additional embodiments are related to lens assemblies that are easy to use and allow quick changing or replacing of the lens assemblies in the field. The lens assemblies allow the user to change out one lens for a more favorable or different lens based on the conditions at a location, or change out a broken, scratched, dirty or otherwise marred lens quickly and easily. This allows a user to quickly resume activities in a safe way.

Figure 1:
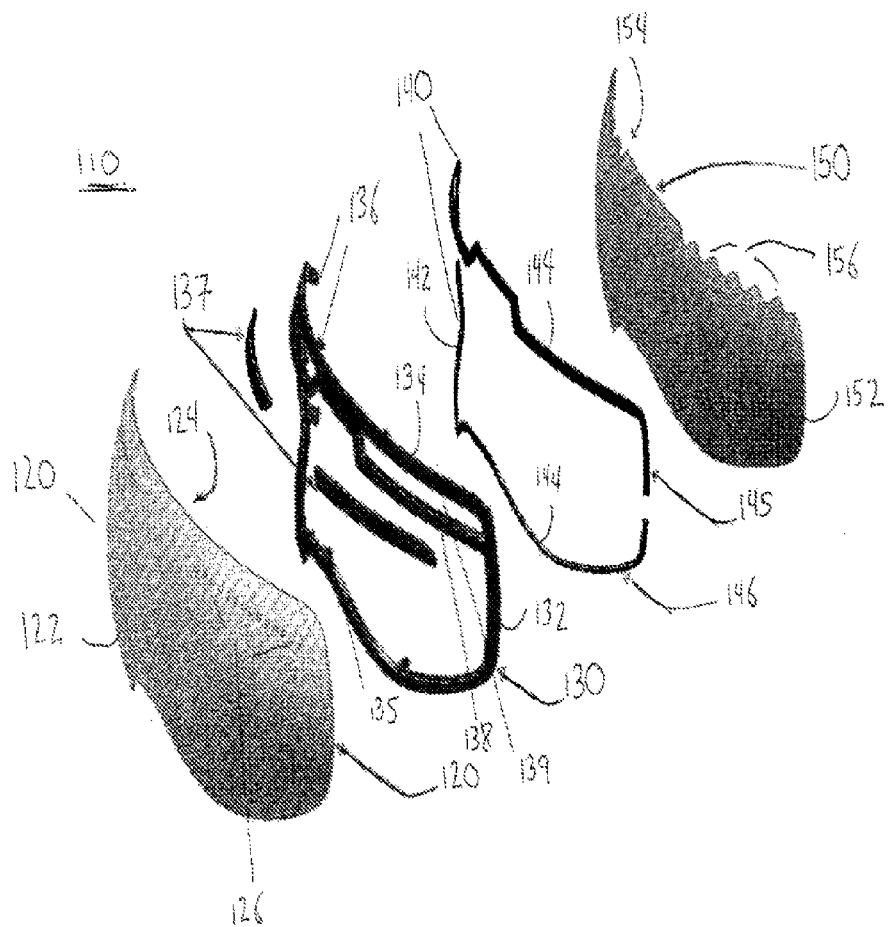
FIG. 1 illustrates an exploded view of an embodiment of a lens assembly.

An exploded view of a lens assembly according to an illustrative embodiment is described with reference to FIG. 1. As illustrated in FIG. 1, the lens assembly is an enhanced view double lens assembly 110 adapted to be coupled, in a removable manner, to a frame 210 (illustrated in FIG. 8) associated with a goggle assembly 200 (illustrated in FIG. 8). The lens assembly 110 includes a first lens or an outer lens 120, a lens bracket 130, a second lens or an inner lens 150 and an outer lens/inner lens spacing apparatus or spacer 140. The outer lens 120 includes a first surface or an outer surface 122 which may be exposed to the atmosphere or ambient elements, and a second surface or an inner surface 124 opposite the outer surface 122 which interfaces with the lens bracket 130. The outer lens 120 may also include one or more venting apertures 126 which extend from the outer surface 122 to the inner surface 124 and may be disposed or located in various locations on the outer lens 120. In the illustrative embodiment of FIG. 1, the one or more venting apertures 126 are located in a top portion of the outer lens 120.

The lens bracket 130 is coupled or attached to the inner surface 124 of the outer lens 120, for example, by a hot melt adhesive, or other coupling means of the type. In an illustrative embodiment, the lens bracket 130 is disposed on one or more peripheral edges of the inner surface 124 of the outer lens 120. The lens bracket 130 is also designed and shaped to frame around the one or more peripheral edges (top, bottom, and sides) of the inner surface 124 of the outer lens 120 minimizing the amount of the lens bracket 130 occluding a user's field of vision through the outer lens 120 when compared to enclosing the lens within a frame. This lens bracket 130 design provides the user with an enhanced visual field of view, including an increased peripheral viewing range, through the outer lens 120. The coupling or attaching of the lens bracket 130 to the inner surface 124 of the outer lens 120 also reduces the profile of the lens assembly 110 and the amount of material used when compared to enclosing the lens within a frame, and provides for a frameless design aesthetic. The lens bracket 130 has a first coupling surface or an outer lens coupling surface 132 and a second coupling surface or a goggle coupling surface 134 opposite the outer lens coupling surface 132. The outer lens coupling surface 132 couples to the inner surface 124 of the outer lens 120.

Additionally, in some embodiments the lens bracket 130 may include one or more venting aperture brackets 138 integrated into the lens bracket 130. The one or more venting aperture brackets 138 form one or more bracket venting spaces 139 around at least a portion of the one or more venting apertures 126. A lens vent foam or absorptive material 137 may be placed within the one or more bracket venting spaces 139.

Figure 6:
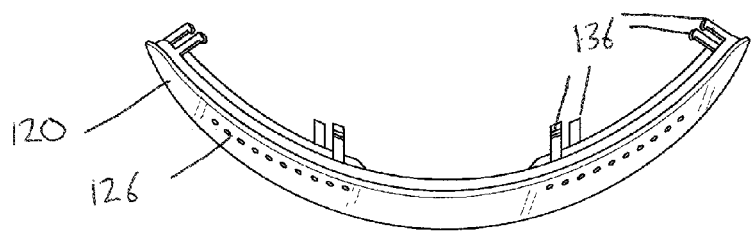
FIG. 6 illustrates a top elevation view of the lens assembly illustrated in FIGS. 2-5.
Figure 7:
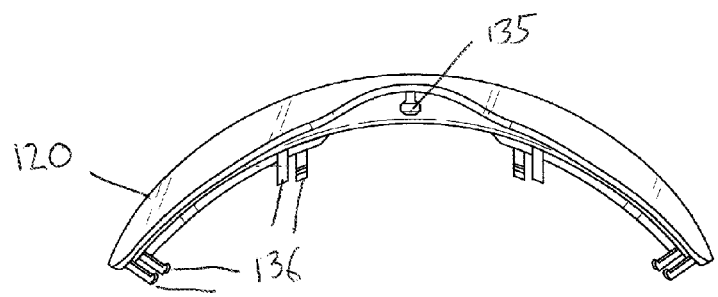
FIG. 7 illustrates a bottom elevation view of the lens assembly illustrated in FIGS. 2-6.
Figure 8:
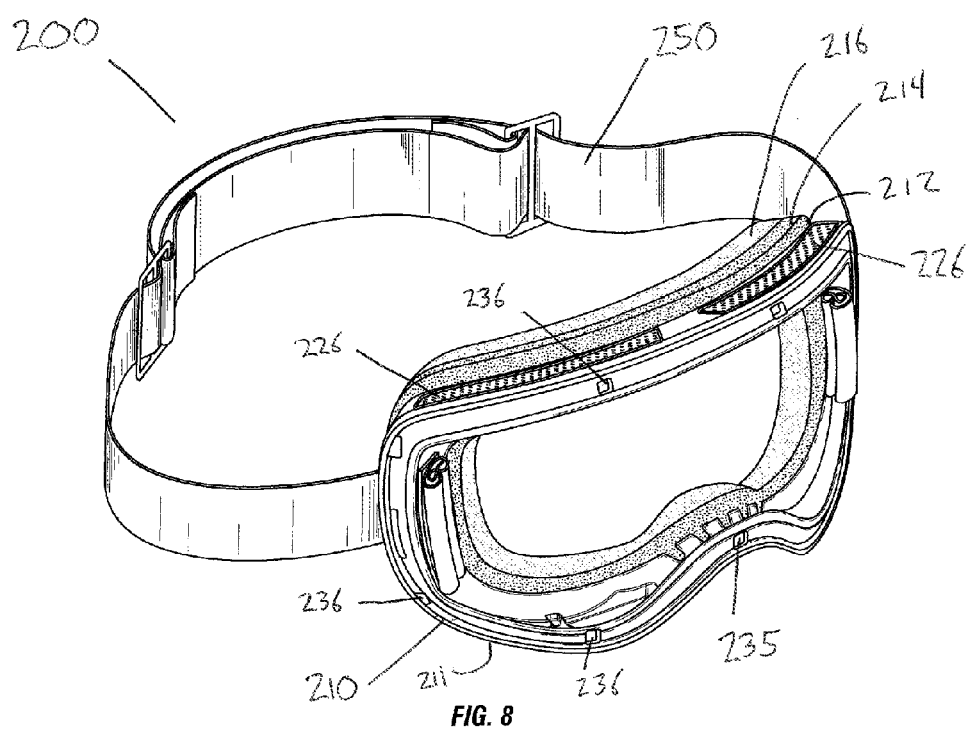
FIG. 8 illustrates a perspective view of an embodiment of a goggle without the lens assembly.
Figure 24:
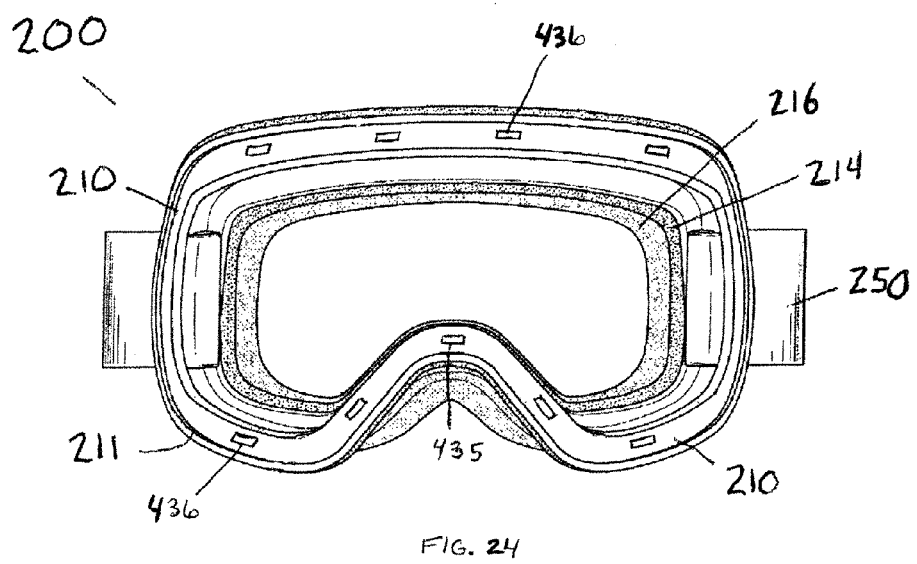
FIG. 24 illustrates a elevation view of another embodiment of the goggle including second magnetic coupling portions.

The lens bracket 130 may also include one or more first connection portions and one or more second connections portions adapted to mate with one or more first coupling points and one or more second coupling points, respectively, on the goggle frame 210 (for example, illustrated in FIGS. 8 and 24). In this illustrative embodiment, the one or more first connection portions include one or more first protrusions 135 and the one or more second connection portions include one or more second protrusions 136 disposed or located on the goggle coupling surface 134. The one or more first protrusions 135 and the one or more second protrusions 136 are adapted to mate with the one or more first coupling points, for example, one or more first coupling apertures 235, and the one or more second coupling points, for example, one or more second coupling points 236, respectively, (for example, illustrated in FIG. 8) on the goggle frame 210 (for example, illustrated in FIG. 8). The first protrusion(s) 135 is centrally located at a nose area and serves as a nose orientation post and the one or more second protrusions 136 are located around at least a portion of a perimeter of the lens bracket 130 (for example, in the brow area as illustrated in FIGS. 6 and 7).

The spacing apparatus or spacer 140 of the lens assembly 110 couples to the inner surface 124 of the outer lens 120, for example, using an adhesive or other coupling means of the type. In an illustrative embodiment, the spacing apparatus 140 may be a foam tape or other structurally pliable material. The spacing apparatus 140 includes an outer lens coupling surface 142 and an inner lens coupling surface 144 opposite the outer lens coupling surface 142, and two sections including a first spacing section or an upper spacing section 145 and a second spacing section or a lower spacing section 146. The thickness of the spacing apparatus 140 may be about the same as the thickness of the lens bracket 130, allowing the inner lens 150 to couple to the inner lens coupling surface 144 of the spacing apparatus 140 and to smoothly extend over portions of the lens bracket 130 without creating substantial ridges or protrusions.

The outer lens coupling surface 142 is attached or coupled to the inner surface 124 of the outer lens 120, and may be disposed adjacent to or abutting the lens bracket 130. As illustrated in FIG. 1, the upper spacing section 145 extends from about midway up a side perimeter of the outer lens 120 and along at least a portion of a top perimeter of the outer lens 120. In embodiments where the lens bracket 130 does not include a venting aperture bracket 138 integrated into the lens bracket 130, the upper spacing section 145 may be shaped to allow the upper spacing section 145 to substantially abut the lens bracket 130, except at a top portion where the upper spacing section 145 may be shaped to form a venting bracket (not shown) which brackets a venting space similar to the venting space 139 around at least a portion of the venting apertures 126. A lens vent foam or absorptive material 137 may also be placed within the bracket venting space.

Similar to the upper spacing section 145, the outer lens coupling surface 142 of the lower spacing section 146 is attached or coupled to the inner surface 124 of the outer lens 120, and may be disposed adjacent to or abutting the lens bracket 130. As illustrated in FIG. 1, the lower spacing section 146 extends from about midway down the side perimeter of the outer lens 120 and along at least a portion of a bottom perimeter of the outer lens 120.

The lens assembly 110 also includes the inner lens 150 which may be smaller than the outer lens 120 and can be sized and shaped to reside within the periphery of the perimeter of the lens bracket 130. The inner lens 150 includes a first surface or a non-user surface 152 which attaches or couples to the spacing apparatus 140 at the inner lens coupling surface 144, for example, using an adhesive or other coupling means of the type, and a second surface or a user surface 154 which is the surface closest to the user's face. The peripheral edges of the non-user surface 154 attaches or couples to the inner lens coupling surface 144 of the spacing apparatus 140 mainly around a periphery of the inner lens 150, except at the top portion where the inner lens 150 includes one or more venting ridges 156 which at least partially extend over the bracket venting space 139 and aid in securing the lens vent foam or absorptive material 137 within the bracket venting space 139.

Figure 2:
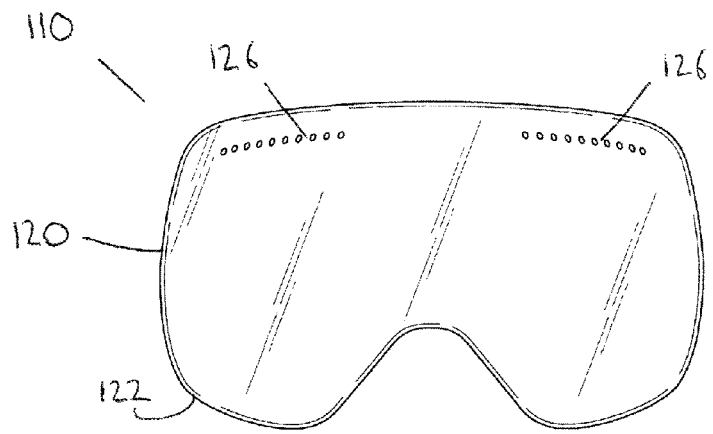
FIG. 2 illustrates a first-side elevation view of an embodiment of the lens assembly.

A first-side elevation view of the lens assembly 110 illustrating the outer surface 122 of the outer lens 120 is described with reference to FIG. 2. As illustrated in FIG. 2, the lens assembly 110 is illustrated as being substantially curvilinear. This substantially curvilinear shape of the lens assembly 110 allows the lens assembly 110 to wrap around at least a portion of the user's face to provide the user with an increased peripheral viewing range. Although, it should be appreciated that angled and flat shaped lenses may also be used. Some of the features illustrated in FIG. 2 include the outer surface 122 of the outer lens 120 and the one or more venting apertures 126 which extend from the outer surface 122 to the inner surface 124 (for example, illustrated in FIG. 1) of the outer lens 120. Although the venting apertures 126 are illustrated as circular in shape, the venting apertures 126 may be any geometric shape that allows the venting of air from the users face (not shown) to the surrounding atmosphere of a goggle assembly 200 (for example, illustrated in FIG. 8) allowing the lens assembly 110 to maintain a clear visual field.

Figure 3:
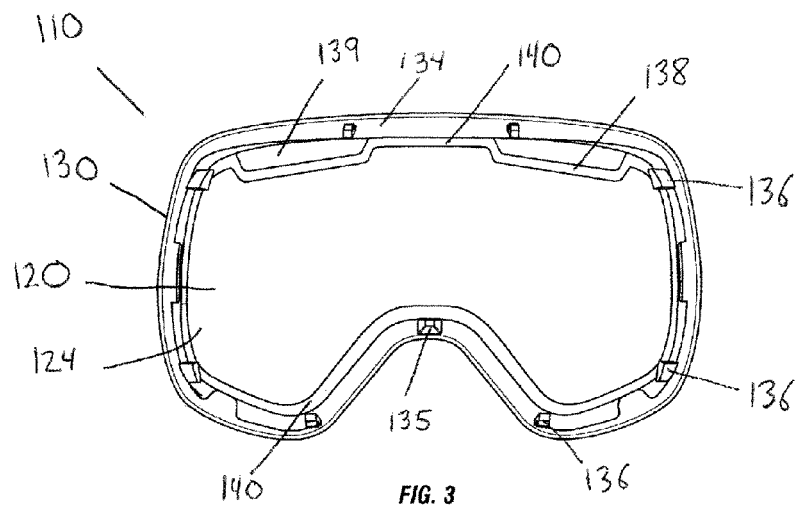
FIG. 3 illustrates a second-side elevation view of an embodiment of the lens assembly illustrated in FIG. 2.

A second-side elevation view of the lens assembly 110 illustrating a side of the lens assembly facing a user is described with reference to FIG. 3. As illustrated in FIG. 3, the lens bracket 130 is disposed around the perimeter of the lens assembly 110. The lens bracket 130 is designed and shaped to frame around the peripheral edges of the outer lens 120 allowing the visual field of view to be enhanced by maximizing a user's field of vision through the outer lens 120. The present view of the lens bracket 130 illustrates the goggle coupling surface 134 and the one or more venting aperture brackets 138. The one or more venting aperture brackets 138 bracket or form one or more bracket venting spaces 139 around at least a portion of the one or more venting apertures 126 (for example, illustrated in FIG. 2). The lens bracket 130 also includes the one or more first protrusions 135 and the one or more second protrusions 136 on the goggle coupling surface 134 which are adapted to mate with the one or more first coupling apertures 235 and the one or more second coupling apertures 236, respectively, (for example, illustrated in FIG. 8) on the goggle frame 210 (for example, illustrated in FIG. 8). As illustrated in FIG. 3, the spacing apparatus 140 is attached or coupled to the inner surface 124 of the outer lens 120 and disposed adjacent to the lens bracket 130.

Figures 4, 5:
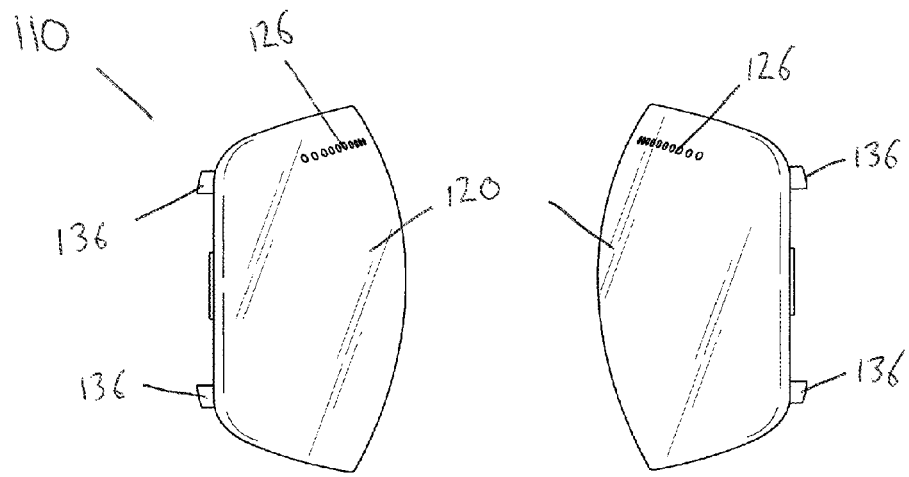
FIG. 4 illustrates a third-side elevation view of the lens assembly illustrated in FIGS. 2 and 3.
FIG. 5 illustrates a fourth-side elevation view of the lens assembly illustrated in FIGS. 2-4.

Various side elevation views and top and bottom elevation views of the lens assembly 110 are described with reference to FIGS. 4-7. As illustrated in FIGS. 4 and 5, the one or more venting apertures 126 are apparent on the outer lens 120, and a portion of the one or more second protrusions 136 are also illustrated. As illustrated in FIG. 6, the one or more venting apertures 126 are apparent on the outer lens 120, and a portion of the one or more second protrusions 136 are also illustrated. As illustrated in FIG. 7, the one or more first protrusions 135, and a portion of the one or more second protrusions 136 are apparent in relation to the lens assembly 110.

Various views of a goggle assembly 200 according to an illustrative embodiment are described with reference to FIGS. 8-14. As illustrated in FIG. 8, the goggle assembly 200 includes a goggle frame 210 including a first side or a lens side 211 adapted to interface with the lens assembly 110 and a second side or a user side 212 which attaches or couples to a middle foam layer 214 and wherein the middle foam layer attaches or couples to a user foam layer 216. The goggle assembly 200 also includes one or more goggle securing straps 250 which attach or couple to the goggle frame 210. Additionally, the goggle frame may include one or more frame venting apertures 226 on one or more of a top portion and a bottom portion of the goggle frame 210.

The lens side 211 of the goggle frame 210 may include the one or more first coupling points and the one or more second coupling points adapted to mate with the one or more first connection portions and one or more second connection portions, respectively, of the lens assembly 110 (for example, illustrated in FIGS. 1-7 and 23). In this embodiment, the one or more first coupling points include the one or more female mating first coupling apertures 235 and the one or more second coupling points include the one or more female mating second coupling apertures 236. The one or more female mating first coupling apertures 235 and the one or more female mating second coupling apertures 236 correspond to and are paired up with the one or more male mating first protrusions 135 and the one or more male mating second protrusions 136, respectively, (for example, illustrated in FIG. 3) of the lens assembly 110 (for example, illustrated in FIGS. 1-7) to couple the lens assembly 110 to the goggle frame 210. The first coupling aperture(s) 235 is located or positioned at a nose area of the goggle assembly 200 and serves as a nose orientation aperture designed to mate with the first protrusion(s) 135 (for example, illustrated in FIG. 3) of the lens assembly 110 (for example, illustrated in FIGS. 1-7). The one or more second coupling apertures 236 are located or positioned around a perimeter of the lens side 211 of the goggle frame 210 and are designed to mate with the one or more second protrusions 136 (for example, illustrated in FIG. 3) of the lens assembly 110 (for example, illustrated in FIGS. 1-7).

Figure 9:
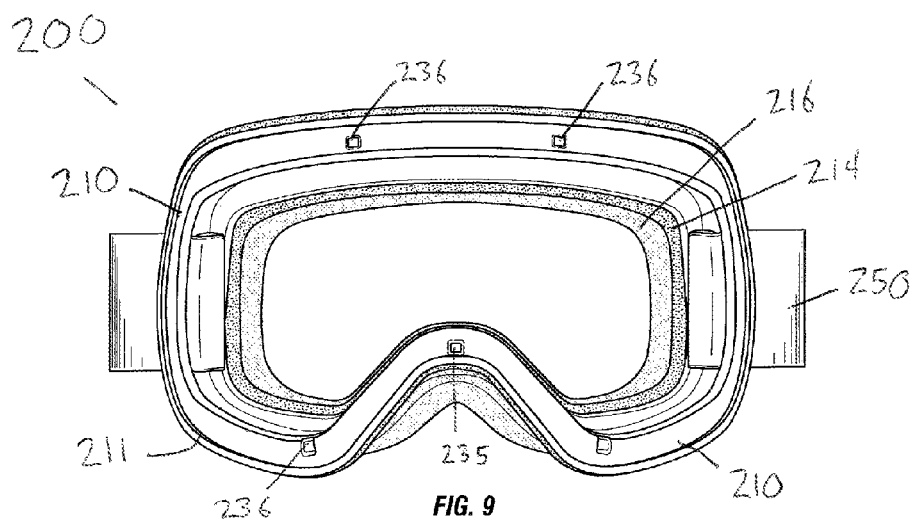
FIG. 9 illustrates a first-side elevation view of the goggle illustrated in FIG. 8.

A first-side elevation view of the goggle frame 210 illustrating the middle foam layer 214 and the user foam layer 216 is described with reference to FIG. 9. In some embodiments, the size relationship of the goggle frame 210 and the foam layers 214 and 216 is such that the foam layers 214 and 216 taper in a direction towards the user and form a funnel type effect. In these embodiments, the user foam portion 216 has a larger peripheral surface area than the middle foam layer 214, and the middle foam layer 214 has a larger peripheral surface area than the goggle frame 210. As illustrated in FIG. 9, the first coupling aperture(s) 235 is centrally located or positioned at the nose area of the goggle assembly 200 and serves as the nose orientation aperture designed to mate with the first protrusion(s) 135 (for example, illustrated in FIG. 3) of the lens assembly 110 (for example, illustrated in FIGS. 1-7), and the one or more second coupling apertures 236 are located or positioned around a perimeter of the lens side 211 of the goggle frame 210 and are designed to mate with the one or more second protrusions 136 (for example, illustrated in FIG. 3) of the lens assembly 110 (for example, illustrated in FIGS. 1-7).

Figure 10:
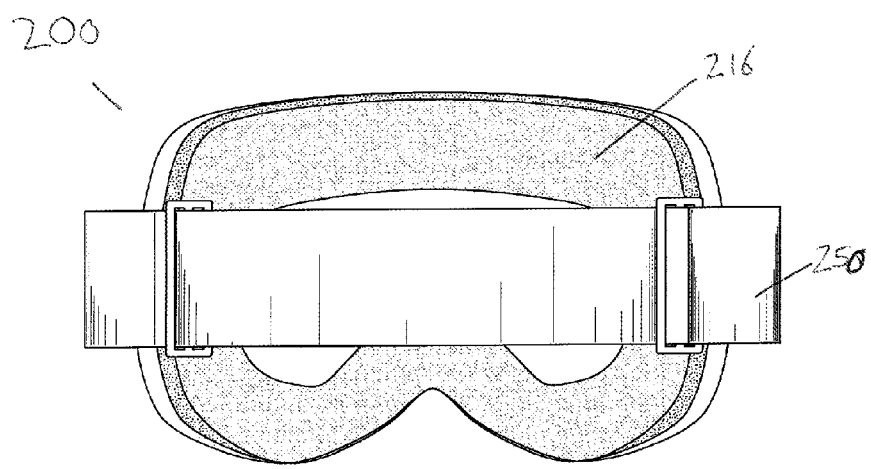
FIG. 10 illustrates a second-side elevation view of the goggle illustrated in FIGS. 8 and 9.

A second-side elevation view of the goggle frame 210 illustrating the user foam layer 216 is described with reference to FIG. 10. In FIG. 10, the large user foam layer 216 and the one or more securing straps 250 are illustrated.

Figure 11:
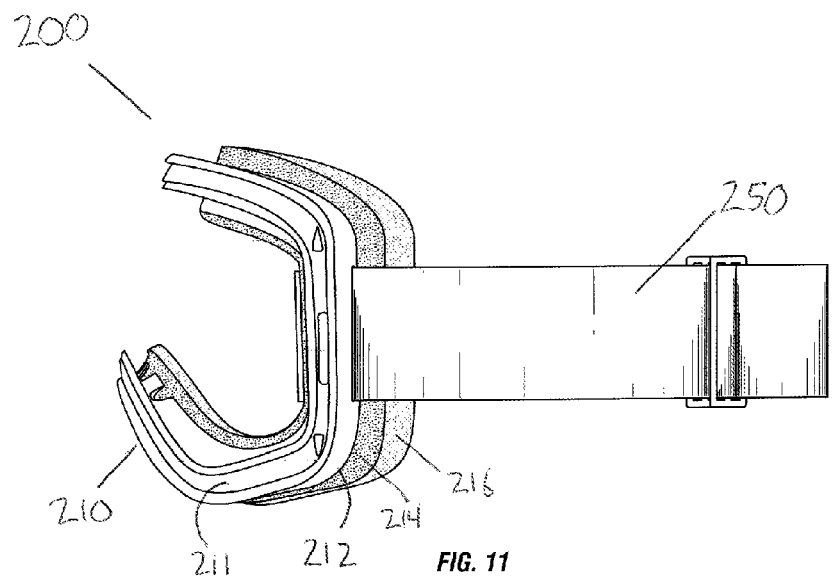
FIG. 11 illustrates a third-side elevation view of the goggle illustrated in FIGS. 8-10.
Figure 12:
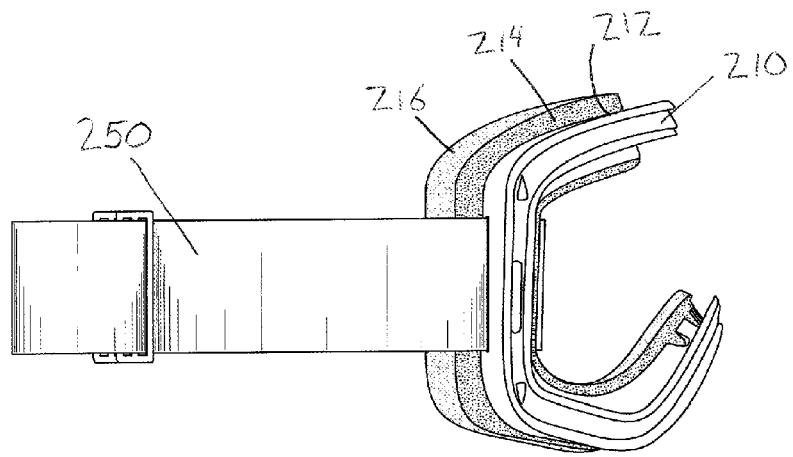
FIG. 12 illustrates a fourth-side elevation view of the goggle illustrated in FIGS. 8-11.

Various side elevation views of the goggle frame 210 are described with reference to FIGS. 11 and 12. In FIGS. 11 and 12, the relationship of the lens side 211 of the goggle frame 210 which interfaces with the lens assembly 110 and the user side 212 which attaches or couples to the middle foam layer 214, and wherein the middle foam layer attaches or couples to the user foam layer 216 is illustrated. Additionally, the one or more goggle securing straps 250 which attach unto the goggle frame 210 is illustrated.

Figure 13:
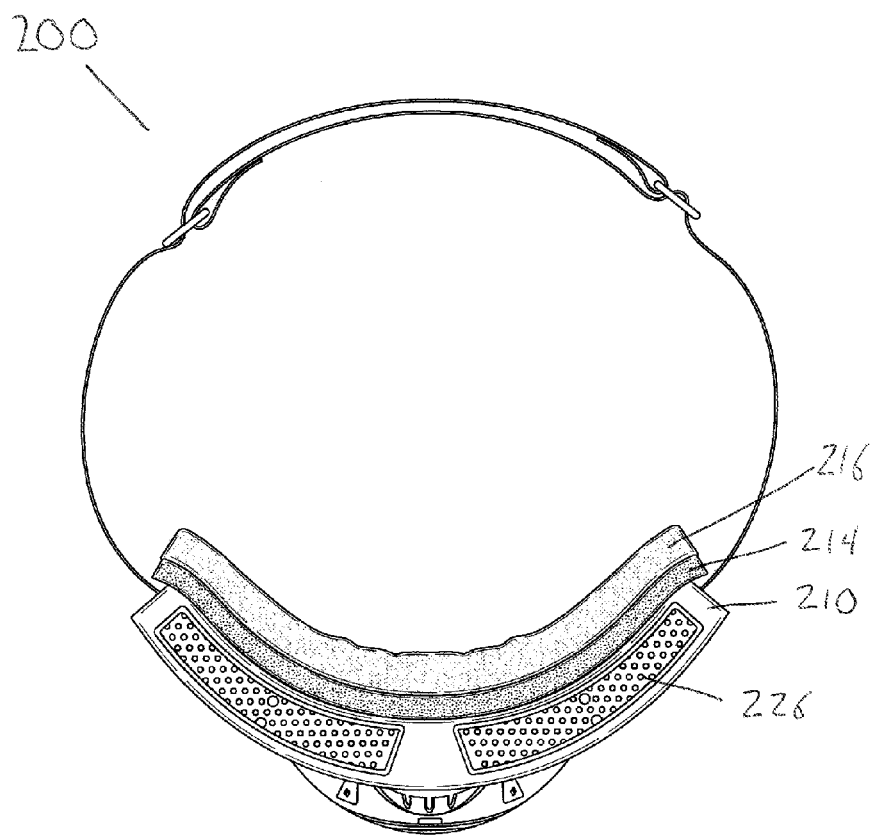
FIG. 13 illustrates a top elevation view of the goggle illustrated in FIGS. 8-12.
Figure 14:
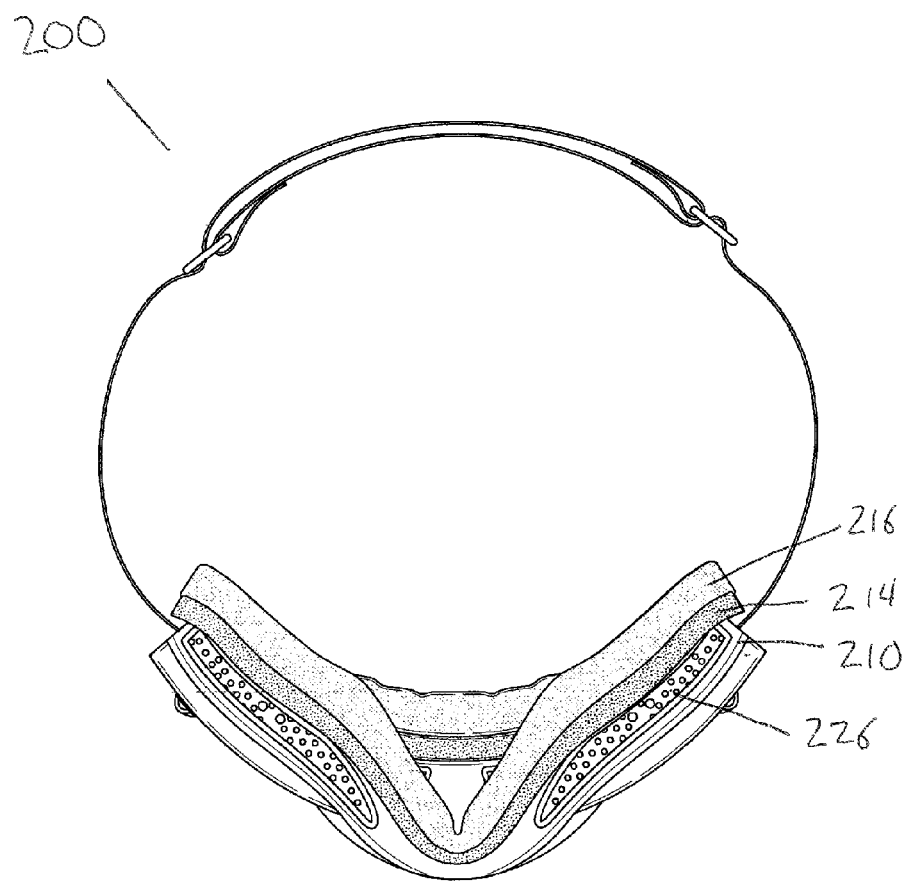
FIG. 14 illustrates a bottom elevation view of the goggle illustrated in FIGS. 8-13.

Top and bottom elevation views of the goggle frame 210 are described with reference to FIGS. 13 and 14. In FIG. 13, the frame venting apertures 226 located on the top of the goggle frame 210, and the layering of the goggle frame 210, the middle foam layer 214, and the user foam layer 216 are illustrated. In FIG. 14, the one or more frame venting apertures 226 located on the bottom of the goggle frame 210, and the layering of the goggle frame 210, the middle foam layer 214, and the user foam layer 216 are illustrated.

Figure 15:
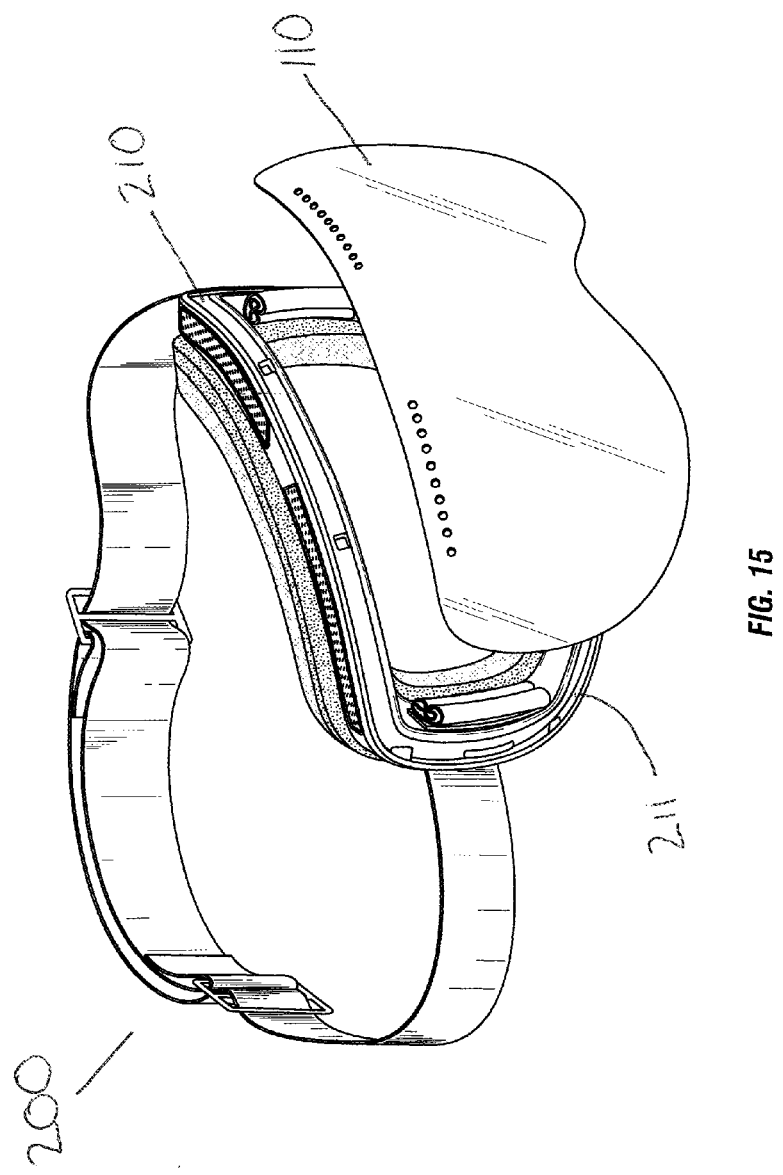
FIG. 15 illustrates a perspective view of the goggle and the lens assembly with the lens assembly illustrated as unattached to the goggle.
Figure 16:
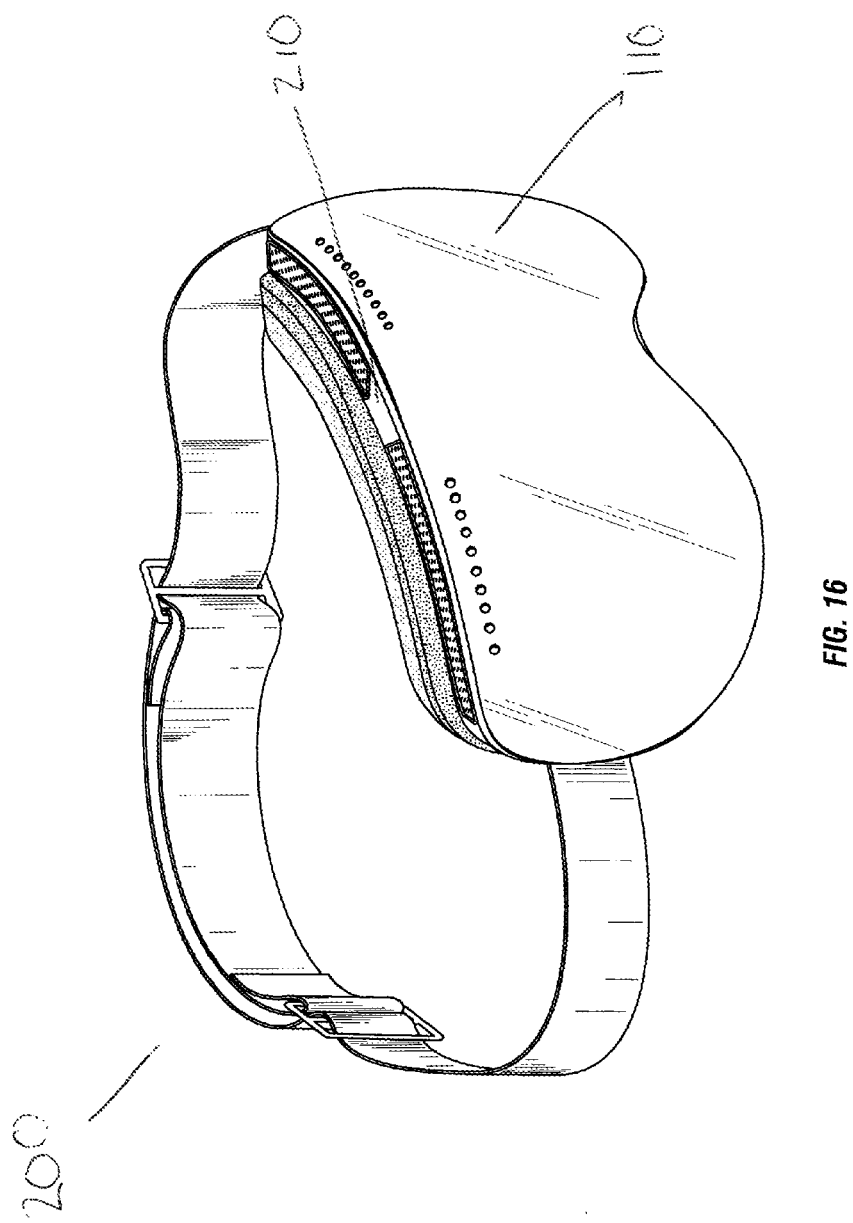
FIG. 16 illustrates a perspective view of the goggle and the lens assembly with the lens assembly illustrated as attached to the goggle.
Figure 17:
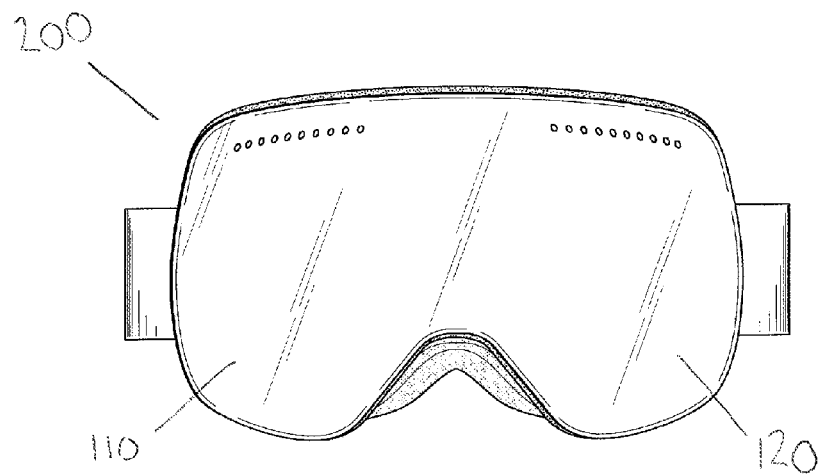
FIG. 17 illustrates a first-side elevation view of the goggle and the lens assembly illustrated in FIG. 16.
Figure 18:
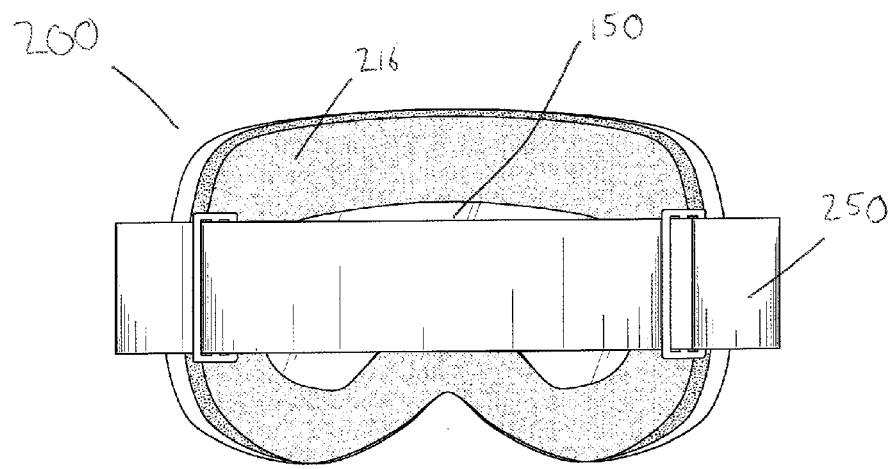
FIG. 18 illustrates a second-side elevation view of the goggle and the lens assembly illustrated in FIGS. 16 and 17.

Various views of the goggle assembly 200 and the lens assembly 110 are described with reference to FIGS. 15-22. A perspective view of the goggle assembly 200 and the lens assembly 110 is illustrated in FIG. 15 with the lens assembly 110 detached from the goggle frame 210, and a perspective view of the goggle assembly 200 and the lens assembly 110 is illustrated in FIG. 16 with the lens assembly 110 coupled to the goggle frame 210. An elevation view of the goggle frame 210 with the lens assembly 110 coupled to the goggle frame 210, wherein the outer lens 120 is most visible, is illustrated in FIG. 17. Another elevation view of the goggle frame 210 with the lens assembly 110 coupled to the goggle frame 210, wherein the user foam layer 216, the inner lens 150, and the one or more securing straps 250 are most visible, is illustrated in FIG. 18.

Figure 19:
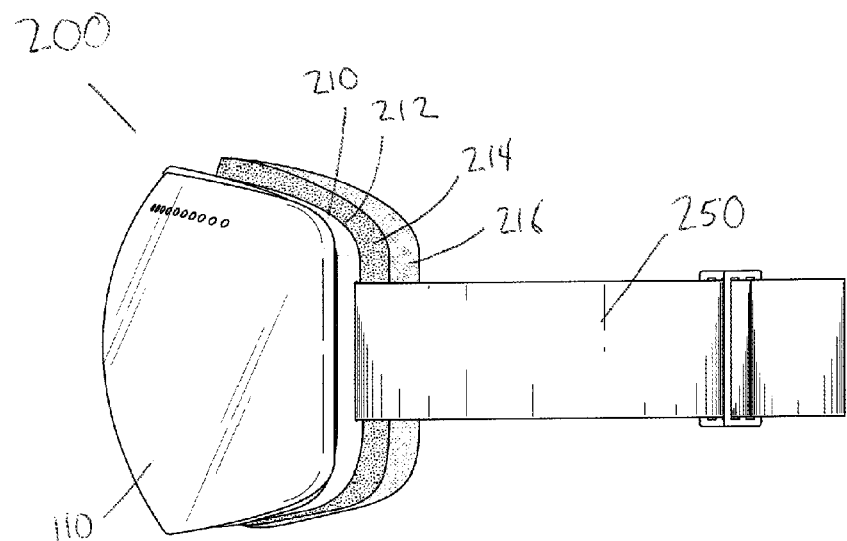
FIG. 19 illustrates a third-side elevation view of the goggle and the lens assembly illustrated in FIGS. 16-18.
Figure 20:
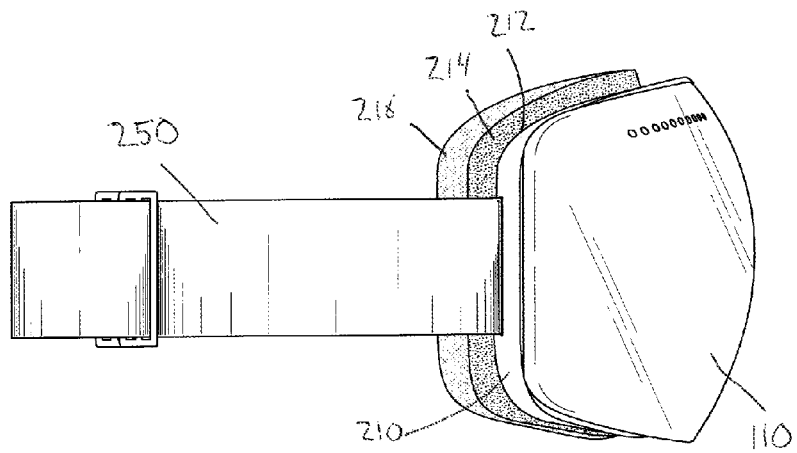
FIG. 20 illustrates a fourth-side elevation view of the goggle and the lens assembly illustrated in FIGS. 16-19.
Figure 21:
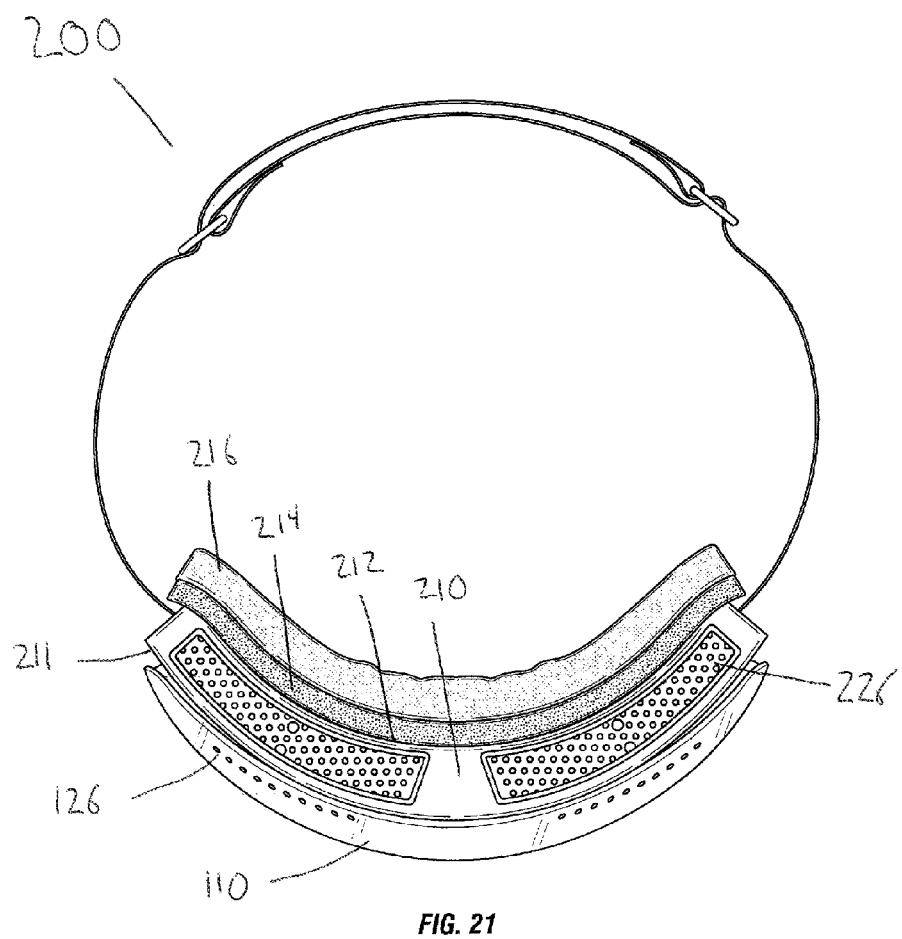
FIG. 21 illustrates a top elevation view of the goggle and the lens assembly illustrated in FIGS. 16-20.
Figure 22:
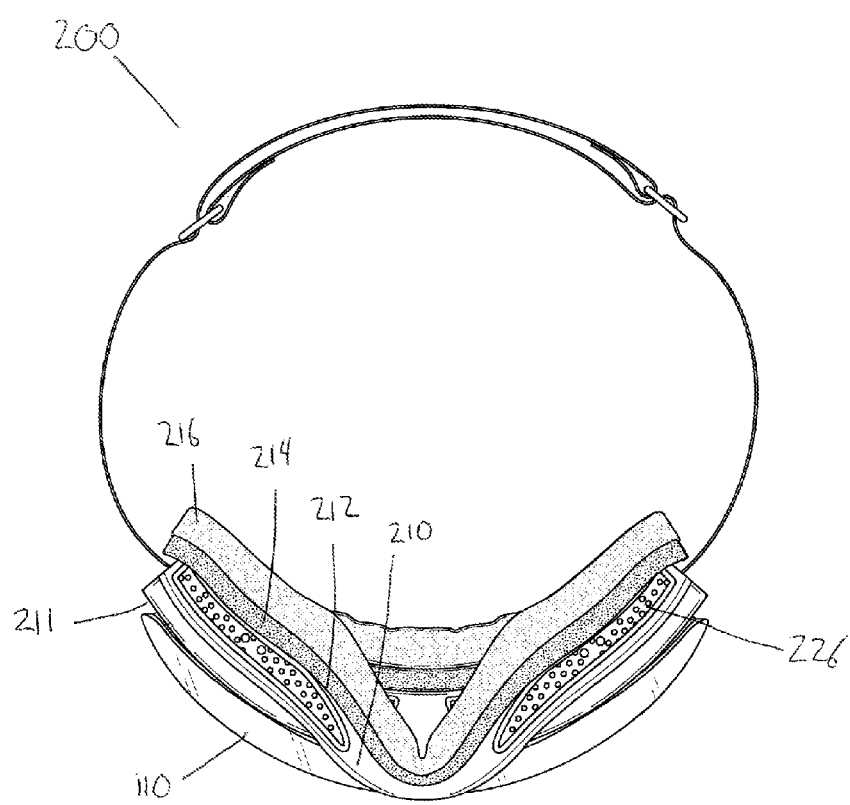
FIG. 22 illustrates a bottom elevation view of the goggle and the lens assembly illustrated in FIGS. 16-21.

Opposing side elevation views of the goggle assembly 200 with the lens assembly 110 attached or coupled to the goggle frame 210 are illustrated in FIGS. 19 and 20. In FIGS. 19 and 20, the relationships of the goggle frame 210 which interfaces with the lens assembly 110, the user side 212 of the goggle frame 210 which attaches or couples to a middle foam layer 214, and the foam layer 216 which attaches or couples to the middle foam layer 214 are illustrated. Additionally, in FIGS. 19 and 20, the one or more goggle securing straps 250 which attach to the goggle frame 210 are illustrated. Top and bottom elevation views of the goggle assembly 200 with the lens assembly 110 attached or coupled to the goggle frame 210 are illustrated in FIGS. 21 and 22. In FIG. 21, the one or more frame venting apertures 226 located on the top of the goggle frame 210, the one or more lens venting apertures 126, and the layering of the goggle frame 210, the middle foam layer 214, and the user foam layer 216 are illustrated. In FIG. 22, the one or more frame venting apertures 226 located on the bottom of the goggle frame 210, and the layering of the user surface of the goggle frame 210, the middle foam layer 214, and the user foam layer 216 are illustrated.

In another illustrative embodiment, the one or more first connection portions and the one or more second connection portions of the lens assembly 110, and the one or more first coupling points and the one or more second coupling points on the goggle frame 210 may be corresponding magnetic couplings adapted to couple the lens assembly 110 to the goggle frame 210. Side elevation views of the lens assembly 110 and the goggle assembly 200 including magnetic couplings are described with reference to FIGS. 23 and 24. In this illustrative embodiment, the one or more first connection portions of the lens assembly 110 include one or more first magnetic portions 335 and the one or more second connection portions of the lens assembly 110 include one or more second magnetic portions 336. Similarly, the one or more first coupling points on the goggle frame 210 include one or more first magnetic portions 435 and the one or more second coupling points on the goggle frame 210 include one or more second magnetic portions 436.

Figure 23:
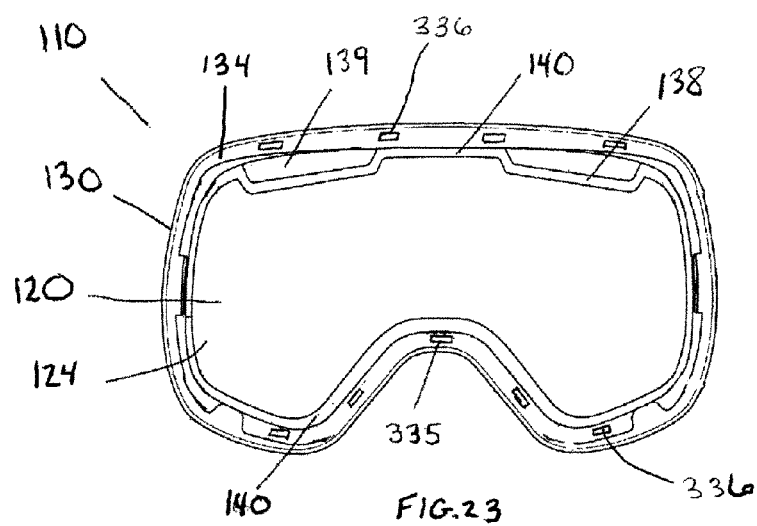
FIG. 23 illustrates a elevation view of another embodiment of the lens assembly including first magnetic coupling portions.

As illustrated in FIG. 23, the one or more first magnetic portions 335 and the one or more second magnetic portions 336 are embedded in the goggle coupling surface 134 of the lens bracket 130. The first magnetic portion(s) 335 may be centrally located at a nose area and serve as a nose orientation magnetic portion and the one or more second magnetic portions 336 may be located around at least a portion of the perimeter of the lens bracket 130. As illustrated in FIG. 24, the one or more first magnetic portions 435 and one or more second magnetic portions 436 are embedded in the lens side 211 of the goggle frame 210. The first magnetic portion(s) 435 may be located or positioned at a nose area of the goggle 200 and serve as a nose orientation magnetic portion designed to mate with or magnetically attract to the one or more first magnetic portions 335 of the lens assembly 110. Similarly, the one or more second magnetic portions 436 may be located or positioned around a perimeter of the lens side 211 of the goggle frame 210 and are designed to mate with or magnetically attract to the one or more second magnetic portions 336 of the lens assembly 110.

Although the embodiments of the lens assemblies are described as being double lens assemblies, the lens assemblies may include only one lens, or more than two lenses. For example, if the lens assembly includes only one lens, the spacing apparatus and the inner lens may be omitted.

Although illustrative embodiments of goggles are described herein, it should be appreciated that in the development of one or more actual embodiments, numerous implementation-specific decisions may be made to achieve specific goals, for example, compliance with system-related and business-related constraints, which may vary from one implementation to another. Moreover, it should be appreciated that a development effort can be complex and time-consuming, but should nevertheless be a routine undertaking for one skilled in the art having the benefit of this disclosure.

Although the goggles have been described and illustrated in connection with certain embodiments, many variations and modifications should be evident to one skilled in the art and may be made without departing from the spirit and scope of the disclosure. The disclosure is thus not to be limited to the precise details of methodology or construction set forth herein as such variations and modification are intended to be included within the scope of the disclosure. Moreover, unless specifically stated any use of the terms first, second, etc. do not denote any order or importance, but rather the terms first, second, etc. are merely used to distinguish one element from another. Accordingly, the disclosure is limited only by the following claims.

What is claimed is:

1. An interchangeable lens assembly, comprising:
a first lens having a first surface and a second surface opposite the first surface;
a lens bracket having a first coupling surface and a second coupling surface opposite the first coupling surface, the first coupling surface being coupled to the second surface of the first lens on at least a portion of a top peripheral edge, at least a portion of a bottom peripheral edge and at least a portion of the side peripheral edges of the second surface of the first lens;
at least one connection portion disposed around at least a portion of a perimeter of the second coupling surface of the lens bracket and adapted to couple to a corresponding coupling point on a goggle; and
a second lens coupled to the second coupling surface of the lens bracket, wherein the at least one connection portion releasably couples the first lens and the second lens to the goggle.

2. The interchangeable lens assembly of claim 1, in which the at least one connection portion includes at least one magnetic portion adapted to couple to the corresponding coupling point on the goggle by a magnetic interaction.

3. The interchangeable lens assembly of claim 1, in which the at least one connection portion includes at least one protrusion adapted to couple to the corresponding coupling point on the goggle.

4. The interchangeable lens assembly of claim 1, in which the first lens includes venting apertures extending through the first lens from the first surface to the second surface.

5. The interchangeable lens assembly of claim 1, further comprising a spacer disposed between the first lens and the second lens and adapted to couple the second lens to the second surface of the first lens.

6. The interchangeable lens assembly of claim 4, in which the lens bracket includes at least one venting aperture bracket adapted to form at least one bracket venting space around at least a portion of the venting apertures.

7. The interchangeable lens assembly of claim 6, further comprising a vent foam disposed within the at least one bracket venting space.

8. The interchangeable lens assembly of claim 1, in which the at least one connection portion includes:
at least one first connection portion disposed at a nose area of the perimeter of the second coupling surface of the lens bracket; and
at least one second connection portion disposed around at least the portion of the perimeter of the second coupling surface of the lens bracket.

9. The interchangeable lens assembly of claim 1, in which the lens bracket is disposed on a peripheral edge of the second surface of the first lens.

10. A goggle for use with an interchangeable lens assembly, comprising:
a goggle frame including a first side adapted to interface with an interchangeable lens assembly and a second side;
a plurality of coupling points disposed on the first side of the goggle frame;
a foam layer coupled to the second side of the goggle frame; and an interchangeable lens assembly comprising:
a first lens having a first surface and a second surface opposite the first surface;
a lens bracket having a first surface and a second surface opposite the first surface, the bracket first surface being coupled to the first lens second surface, and
a second lens coupled to the lens bracket second surface, wherein the bracket comprises a plurality of connectors extending from the lens bracket second surface,
at least one first connector is disposed at a nose area of a perimeter of the second coupling surface of the lens bracket, and
each one of the plurality of connectors is adapted to be releasably received by a respective one of the plurality of coupling points so that interaction of the plurality of connectors with the plurality of coupling points releasably couples the interchangeable lens assembly to the first side of the goggle frame.

11. The goggle of claim 10, in which the at least one coupling point includes at least one magnetic portion adapted to couple to the corresponding connection portion of the interchangeable lens assembly by a magnetic interaction.

12. The goggle of claim 10, in which the plurality of coupling points includes a plurality of apertures each adapted to receive and couple to a respective corresponding coupling point of the interchangeable lens assembly.

13. The goggle of claim 10, in which the foam layer further comprises a middle foam layer coupled to the second side of the goggle frame and a user foam layer coupled to the middle foam layer opposite the goggle frame.

14. The goggle of claim 10, in which the goggle frame includes one or more frame venting apertures disposed on a perimeter of the goggle frame.

15. The goggle of claim 10, further comprising a securing strap coupled to the goggle frame.

16. An eyewear device, comprising:
a first lens having a first surface and a second surface opposite the first surface;
a lens bracket having a first coupling surface and a second coupling surface opposite the first coupling surface, the first coupling surface being coupled to the second surface of the first lens;
a plurality of rearwardly extending connection portions spaced around at least a portion of a perimeter of the second coupling surface of the lens bracket;
a frame including a first side and a second side opposite the first side; and
a plurality of coupling points disposed on the first side of the frame, each of the plurality of coupling points being adapted to couple to a respective one of the plurality of rearwardly extending connection portions on the lens bracket to releasably couple the first lens to the frame first side,
wherein a first one of the plurality of rearwardly extending connection portions is positioned at one of a nose area or a brow area of the perimeter of the second coupling surface of the lens bracket; and
wherein the lens bracket is positioned intermediate the first lens and the frame.

17. The eyewear device of claim 16, in which the at least one coupling point and the at least one connection portion are corresponding magnetic portions adapted to couple to each other by a magnetic interaction.

18. The eyewear device of claim 16, in which at least one rearwardly extending connection portion includes at least one protrusion, and at least one coupling point includes at least one aperture adapted to receive and couple to the at least one protrusion.

19. The eyewear device of claim 16, further comprising a second lens and a spacer, the spacer being disposed between the first lens and the second lens and adapted to couple the second lens to the second surface of the first lens.

20. The eyewear device of claim 16, further comprising a foam layer coupled to the second side of the frame.

21. The eyewear device of claim 16, in which the lens bracket is disposed on a peripheral edge of the second surface of the first lens.

* * * * *